United States Patent [19]

Badrinath

[11] Patent Number: 5,207,753
[45] Date of Patent: May 4, 1993

[54] BONE FRACTURE REPAIR APPARATUS AND METHOD

[76] Inventor: Kannivelu Badrinath, 18 Taunton Close, Hainault, Essex, IG6 3DN, England

[21] Appl. No.: 834,893

[22] Filed: Feb. 11, 1992

[30] Foreign Application Priority Data

Feb. 18, 1991 [GB] United Kingdom ............ 9103345
May 3, 1991 [GB] United Kingdom ............ 9109623
Oct. 16, 1991 [GB] United Kingdom ............ 9121930

[51] Int. Cl.[5] ........................................ A61F 2/32
[52] U.S. Cl. .................................................. 606/96
[58] Field of Search ............ 606/60, 65, 66, 72, 606/73, 79, 80, 87, 96, 97, 98, 103, 104

[56] References Cited

U.S. PATENT DOCUMENTS

| 2,235,419 | 3/1941 | Callahan | 606/96 |
| 4,830,000 | 5/1989 | Shutt | 606/80 |
| 4,865,025 | 9/1989 | Buzzi | 606/96 |
| 4,988,350 | 1/1991 | Herzberg | 606/71 |
| 5,007,911 | 4/1991 | Baker | 606/80 |
| 5,049,150 | 9/1991 | Cozad | 606/96 |
| 5,053,037 | 10/1991 | Lackey | 606/96 |
| 5,067,898 | 11/1991 | Dury | 606/96 |
| 5,078,719 | 1/1992 | Schreiber | 606/96 |
| 5,087,260 | 2/1992 | Fixel | 606/69 |

*Primary Examiner*—Robert A. Hafer
*Assistant Examiner*—Michael Brown
*Attorney, Agent, or Firm*—Harrison & Egbert

[57] ABSTRACT

A bone fracture repair apparatus comprises a guide having three parallel elongate bores two of which are small diameter for receiving a guide wire and one of which is of larger diameter for receiving and guiding a screw. the apparatus permits a plurality of screws to be inserted in substantially parallel disposition. By employing a guide wire in a small diameter bore to locate the guide, screws can be inserted in substantially parallel disposition using the larger diameter bore as a guide and using the guide wire as a pivot to change the position for inserting of a screw.

6 Claims, 6 Drawing Sheets

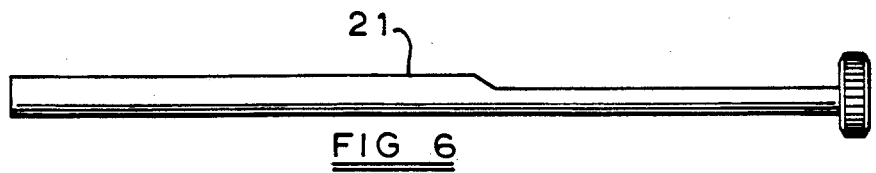
FIG 6
FIG 7
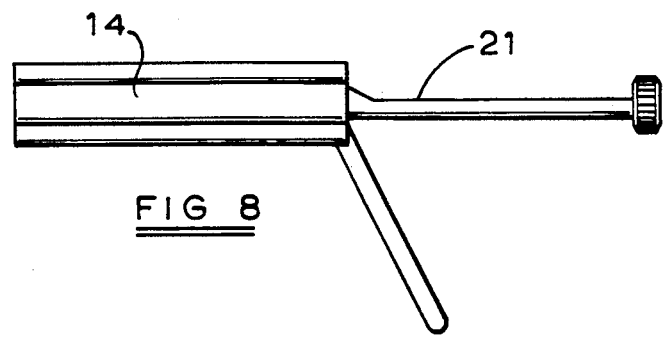
FIG 8
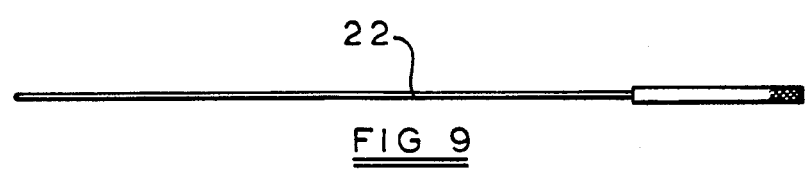
FIG 9
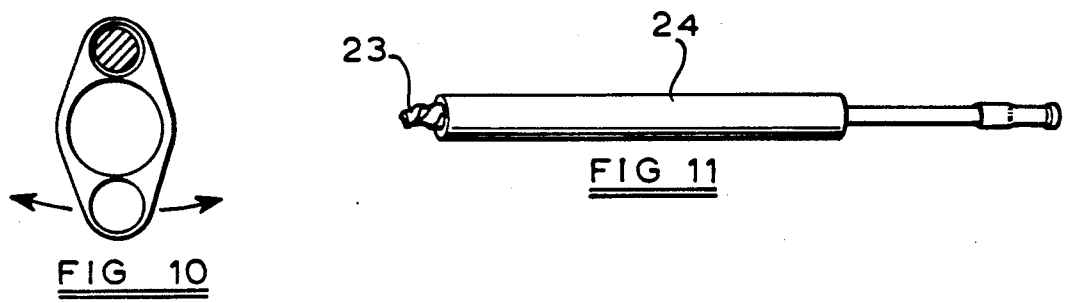
FIG 10
FIG 11

BONE FRACTURE REPAIR APPARATUS AND METHOD

This invention relates to the repair of bone fractures and more particularly but not solely to the repair of fractures of the neck of the femur.

BACKGROUND OF THE INVENTION

The hip joint is a ball and socket joint. The acetabular cavity of the Pelvis forms the socket and the head of the femur forms the ball part of the joint. The head of the femur (the upper end) is connected to the main shaft of the femur through its neck.

Fractures sustained through the neck of the femur are often difficult to treat as they lie within the joint and do not heal easily.

Post-operative complications like collapse of the bone at the fracture site, non-union of the fracture and avascular necrosis of the head of femur are also common. This is because of the nature of blood supply at this region.

PRIOR ART

For many years surgeons have been devising various means of fixing fractures of the neck of femur. If an intra-capsular fracture is suitable for fixation most surgeons currently use two or three screws of one type or another for the procedure.

The method of fixing these fractures varies from hospital to hospital and surgeon to surgeon. However, the general principle has remained the same—to reduce the fracture accurately using x-ray imaging and then pass a guide wire through the neck of the femur across the fracture site into the head of the femur. This is checked by x-ray again and if the position is satisfactory, the guide wire is removed and a screw of adequate length is replaced in its position. Two or three screws are used in this way. When the screws are positioned properly and tightened well, the reduced fracture is held securely in place. One of the commonly used screws for this purpose is a 6.5 mm width cancellous screw.

There are considerable difficulties and problems associated with this technique some of which will now be explained.

1. When the guide wire is removed to insert the screw, it is often difficult to find the entry point of the guide wire on the bone unless the area is widely exposed by a longer skin incision. This is particularly so in obese patients.
2. Individual guide wires have to be placed before the second and third screws are used with no accurate control of where the second and third guide wires would lie in relation to the first. This in turn means that there is no control where the second and third screws would finally lie in relation to the first screw. The procedure may therefore take a longer time as the different guide wires have to be positioned individually and the surgeon has to use his skill every time a guide wire is introduced to place it at the right position and again when it is replaced by a screw.
3. When the guide wires lie within the bone there is no accurate or definitive method available to measure the depth to which the guide wires have been pushed into the bone. The required length of screw that should replace the guide wire is therefore calculated by various indirect methods.

To overcome the difficulty of positioning the screws where the guide wires lie accurately, some manufacturers have introduced cannulated screws. These screws can be slid over the guide wire and screwed into position over it. When the wire is removed, the screw remains in the position where the guide wire had been.

Disadvantages of Using Cannulated Screws (a) The cannulated screws are more expensive—often 3 times as expensive as ordinary cancellous screws.
(b) The guide wire should be fairly thin to allow small diameter screws to be used adding to the risk of guide wire breakage within the bone. Also the thin guide wires bend easily when they are being driven into the bone.
(c) If thicker and stronger guide wires are used, the diameter of the cannulated screw which would slide over them has to increase correspondingly.
(d) There is still no control where the second and third guide wires would lie in relation to the first guide wire/screw and therefore no control over the position of the second and third screws in relation to the first.

SUMMARY OF THE INVENTION

The present invention seeks to provide an apparatus and a method that simplifies the repair of bone fractures and which overcomes at least some of the previously mentioned problems.

According to one aspect of the invention there is provided a bone fracture repair apparatus comprising a guide having three parallel elongate bores two of which are small diameter for receiving a guide wire and one of which is of larger diameter for receiving and guiding a screw.

The apparatus may include a pair of guide wires of diameter which permits a snug sliding fit in said bores of smaller diameter of the guide.

A second guide of elongate substantially cylindrical cross section may be provided having an outer diameter which permits a snug sliding fit in said bore of larger diameter of the guide and an inside diameter substantially equal to the diameter of said bores of smaller diameter.

Preferably, the second guide is of length greater than the length of the guide and is cut away at or towards one end to reveal the inside of the bore and is calibrated adjacent the revealed portion of the bore, and one of the guide wires is provided with a marker for cooperation with the calibration to indicate the extent by which the guide wire extends beyond the end of the guide.

There may be provided a guide anchoring pin having a portion of length greater than the length of the guide and of diameter which permits a close sliding fit within said bores of smaller diameter and a portion of larger diameter which limits the extension of the pin beyond the bore.

The apparatus may also include a drill of length longer than the guide, of diameter greater than that of the guide wires but substantially less than the diameter of said bore of larger diameter which drill has a sleeve the outer diameter of which permits a guiding fit in said bore of larger diameter and limits the cutting depth of the drill.

The apparatus may further include a tap, of length greater than the length of the guide, of diameter greater than the diameter of the drill but less than the diameter of said bore of larger diameter, which tap has a sleeve the outer diameter of which permits a guiding fit in said bore of larger diameter and is adjustable to determine the limit of threaded depth cut.

At least one additional elongate bore of the smaller diameter may be provided parallel to the three parallel elongate bores.

The guide may be formed from individual cylindrical tubes secured together in parallel side by side disposition or alternatively may comprise a solid bar preferably of oval cross-section with the parallel elongate bores formed therethrough.

According to another aspect of the invention there is provided a method of bone fracture repair in which a plurality of screws are inserted in substantially parallel disposition by employing a guide having a plurality of parallel bores at least one of which is of small diameter and is located on a guide wire of similar diameter inserted substantially centrally through the fracture so as to define the inclination of the screws which are inserted through another one of the bores of larger diameter which serves to guide the screws. the guide employed may comprise three bores two of which are of said small diameter and wherein an anchoring pin is inserted through the second of the two smaller bores into the bone to secure the guide against rotation prior to insertion of each screw.

According to another aspect of the invention there is provided a method of repairing a bone fracture comprising the steps of:

(a) driving a first guide wire substantially centrally of the bone through the fracture (b) sliding onto the first guide wire a guide comprising three parallel elongate bores, two of which are small diameter substantially equal to the diameter of the guide wire and one of which is of larger diameter, by sliding a small bore of the guide over the first guide wire, (c) rotating the guide around this first guide wire so that the bore of larger diameter is directed towards a suitable area to receive a screw (d) introducing into the bore of larger diameter a second guide of elongate substantially cylindrical cross section having an outer diameter which permits a snug sliding fit in the bore, and an inside diameter substantially equal to the diameter of said bores of smaller diameter.

(e) driving a guide wire into the bone through the bore of the second guide and the fracture to a required depth as defined by a monitoring means, (f) noting the required depth, (g) passing a guide anchoring pin through the other bore of small diameter into the bone to secure the guide against rotation, (h) removing the guide wire and second guide from the bore of larger diameter, (i) inserting a screw of length equal to said noted depth through the bore of larger diameter and driving it into the bone, (j) removing the guide anchoring pin, (k) rotating the guide around the first guide wire so that the bore of larger diameter is directed towards another suitable area to receive a screw, and (l) repeat steps (d) to (j).

The method step (i) may include the introduction into the bore of larger diameter a drill having a sleeve which is a snug sliding fit inside the bore and which limits the depth of initial drilling into the bone to facilitate insertion of the screw.

The method step (i) may further include, following the predrilling of the bone, the introduction into the bore of larger diameter a tap having a sleeve which is a close sliding fit inside the bore and which limits the depth of pretapping of a thread into the bone prior to insertion of the screw.

In a specific application of the method, previously defined, for a repair of fracture of the neck of the femur, the guide wire is inserted through an incision into the head of the femur passing substantially centrally through the neck. In this specific application, in step (c) the guide may be rotated so that the bore of larger diameter is directed towards the antero-inferior part of the neck of the femur and in step (g) the anchoring pin may be driven into the outer cortex of the femur to secure the guide against rotation.

BRIEF DESCRIPTION OF THE DRAWINGS

In order that the invention and its various other preferred features may be understood more easily, some embodiments thereof will now be described by way of example only, with reference to the drawings, which relate to the repair of a femur and in which:

FIG. 6 is a side view of a second guide for use with the guides of FIGS. 2 to 4, FIG. 7 is a plan view of the second guide of FIG. 6, FIG. 8 is a side view illustrating the second guide of FIG. 6 inserted in the guide of FIG. 2, FIG. 9 is a side view of a guide anchoring pin for use with the guides of FIGS. 2 to 4, FIG. 10 is an end view of the guide illustrated in FIG. 4, FIG. 11 is a side view of a drill for use with the guide of FIGS. 2 to 4.

DESCRIPTION OF THE PREFERRED EMBODIMENTS

Figure 1:
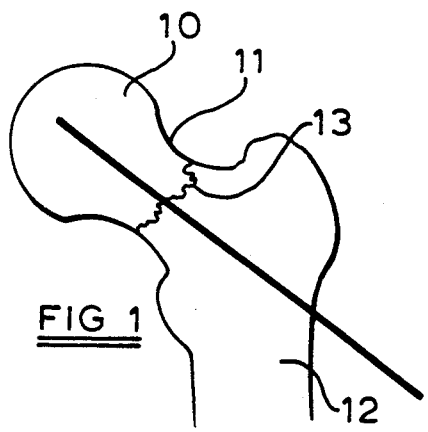
FIG. 1 is an outline schematic drawing of the upper end of a femur.

The femur illustrated in FIG. 1 has a head 10, a neck 11 and a shaft 12 and illustrates a common fracture of the neck at 13. The invention is concerned with securing such a fracture by introducing screws through the neck and head of the femur.

Figure 2:
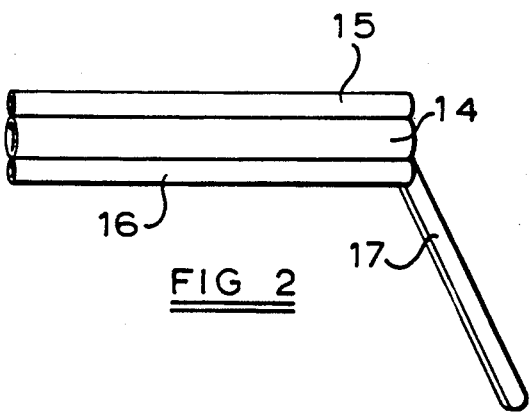
FIG. 2 is a side elevation of a main guide constructed in accordance with the invention.

The guide illustrated in FIG. 2 has three tubes the axis of which are coplanar and parallel. The central tube 14 is of larger diameter than the outer tubes 15 and 16 and has a correspondingly larger bore. The guide is provided at one end with a handle 17. The diameter of the bores and the length of the guide depends upon the size of the screw for which it is intended for use. For the purpose of illustration we will assume that the guide is designed for a 6.5 mm cancellous screw which is the size normally used in adult patients. In such an arrangement the guide the smaller bores measurement would be of length 100 mm, the smaller bores 3.2 mm and the larger bore 8 mm. The 3 mm bore is designed to permit a snug sliding fit of a guide wire or guide anchoring pin whilst the 8 mm bore is just wide enough to allow the head of a 6 mm screw to pass therethrough.

Figure 3:
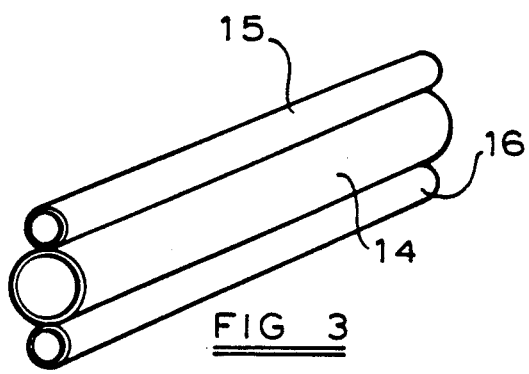
FIG. 3 is an isometric view of the guide illustrated in FIG. 2.
Figure 4:
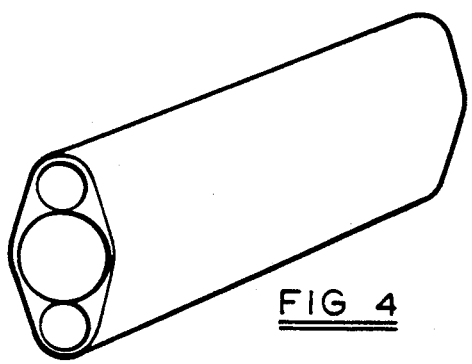
FIG. 4 is an isometric view of an alternative construction of guide similar to that of FIG. 3.

FIG. 4 illustrates an alternative construction of guide similar to FIG. 3 but manufactured from a single rod. Bores of size similar to the bores of the tubes 14, 15 and 16 are provided in parallel disposition through the rod. The guide may have a handle similar to the handle 17 and is useable in a similar manner to that which will be hereinafter described in relation to FIGS. 2 and 3.

Figure 5:
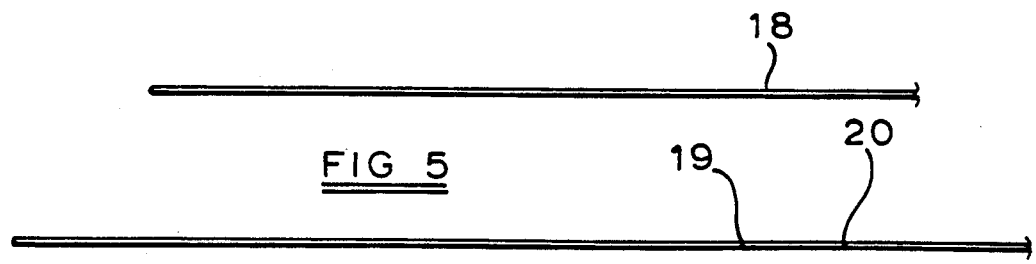
FIG. 5 illustrates a pair of guide wires for use with the guides of FIGS. 2 to 4.

FIG. 5 illustrates a first guide wire 18 measuring 3.2 mm in diameter and 225 mm in length. There is also illustrated a main guide wire 19 the standard size for use in adult patients would measure 3.2 mm in diameter and 350 mm in length. The main guide wire is provided with a marking for cooperation with a scale on a centering guide as will hereinafter be described.

FIGS. 6 and 7 illustrate a second or centering guide 21 which is elongate and of cylindrical cross section having an outside diameter substantially equal to the diameter of the bore of the central tube 14 to permit sliding insertion therein. The size for use in the standard guide is 200 mm in length and 7.8 mm in diameter which is approximately the same diameter as the screw head of a 6.5 mm screw. The bore of the guide 21 is again 3.2 mm in diameter to permit the main guide wire 19 to slide therein. The distal half of the second guide 21 is cut away so that it is only a half cylinder thereby exposing the bore within. When the main guide wire passes through the bore it is visible in this section so that the marking 20 can be seen. Adjacent to the exposed bore on the guide 21 there is a scale in millimeters marked on the flat cut surface.

FIG. 8 shows the second guide 21 inserted in the bore of the central tube 14 from which it can be seen that the distal end with the calibration extends outside the bore.

FIG. 9 is a guide anchoring pin which is of length 160 mm of which the proximal 130 mm is of 3.2 mm in diameter with a pointed end and the distal 30 mm is of 5 mm diameter with the outer surface scored for grip. When this pin is pushed fully through a small bore in one of the outer tubes 16 it extends beyond the end of the guide by 30 mm and is used for stabilising the guide as will hereinafter be described.

FIG. 10 illustrates an end view of the main guide the outer bore being secured by a guide wire and the arrows being intended to show the rotational capability of the guide.

FIG. 11 illustrates a starting drill 23 for use with the main guide the drill has a sleeve 24 which is intended to be a snug fit in the bore of the tube 14 and defines the maximum drilling depth. This drill is only to open the outer cortex of the femur after the main guide wire is removed and before the screw is inserted as will be hereinafter described.

Figure 12:
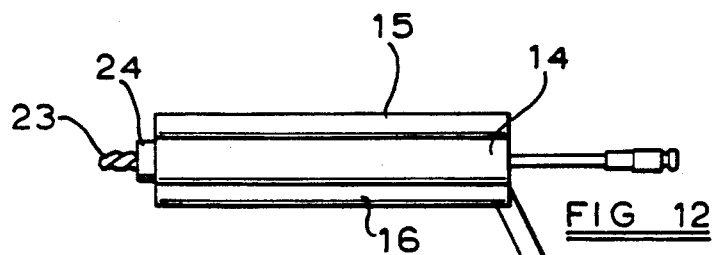
FIG. 12 is a side view illustrating the drill of FIG. 11 inserted in the guide of FIG. 2.

FIG. 12 shows the drill 23 inserted into the central tube 14 of the guide.

Figure 13:
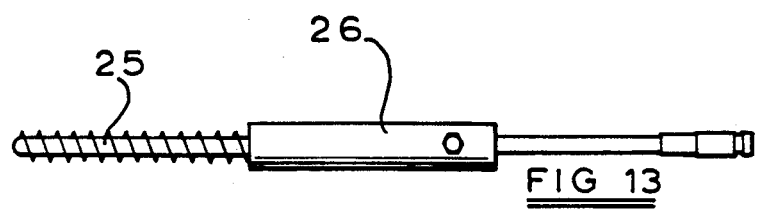
FIG. 13 is a side view of a tap for use with the guide of FIGS. 2 to 4.

FIG. 13 illustrates a tap 25 provided with a sleeve 26 of diameter substantially equal to the diameter of the bore of the tube 14 the sleeve being adjustable on the tap to define the maximum depth of thread that it can produce.

Figure 14:
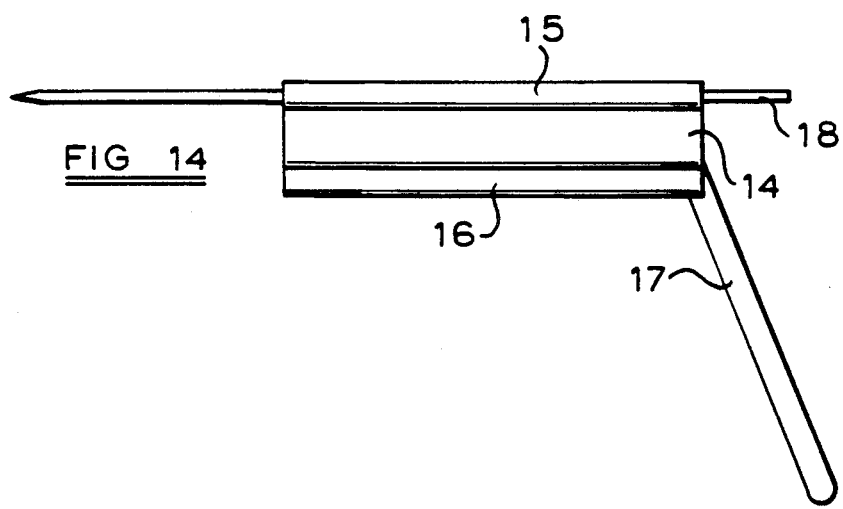
FIG. 14 is a side elevation showing the main guide of FIG. 2 mounted on a guide wire by sliding a small bore of the guide over the wire.

The method of use of the new guide will now be described. The first guide wire 18 is accurately positioned and driven through the neck and head of the femur along the line indicated in FIG. 1 this operation is effected with the help of guidance by x-ray displays showing views in two planes to ensure the central disposition. The main guide is now slid over the guide wire with the wire sliding into the bore of the tube 15, as shown in FIG. 14. With the guide now in position it can rotate freely around the first guide wire as illustrated in FIG. 10. This allows the bore of the central tube 14 to take up different positions on the outer cortex of the femur whilst at the same time maintaining a parallel position to the first guide wire. As has been previously mentioned the diameter of the bore of the central tube 14 closely matches the diameter of the head of the screw that will be used for fixing the fracture. If the screw is driven through this bore into the neck of the femur it would automatically lie parallel to the first guide wire within the head and neck of the femur.

Figure 15:
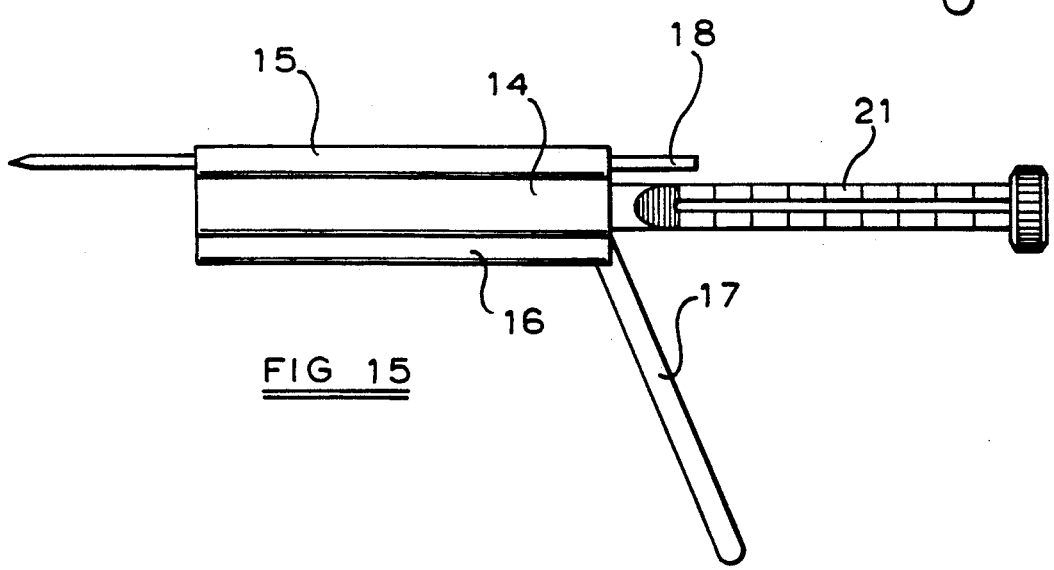
FIG. 15 is a side elevation showing the second guide of FIG. 6 slidably inserted into the main guide.
Figure 16:
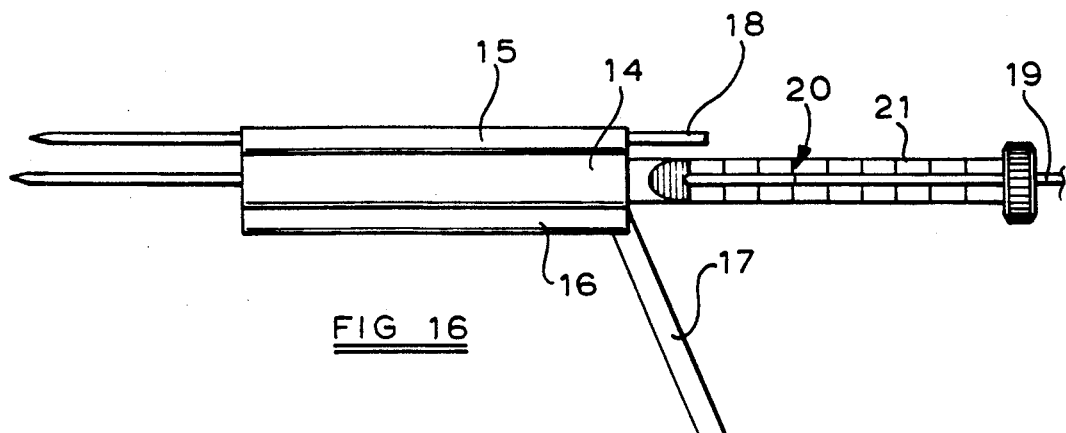
FIG. 16 is a side elevation similar to FIG. 15 but showing the main guide wire of FIG. 5 inserted in the second guide.
Figure 17:
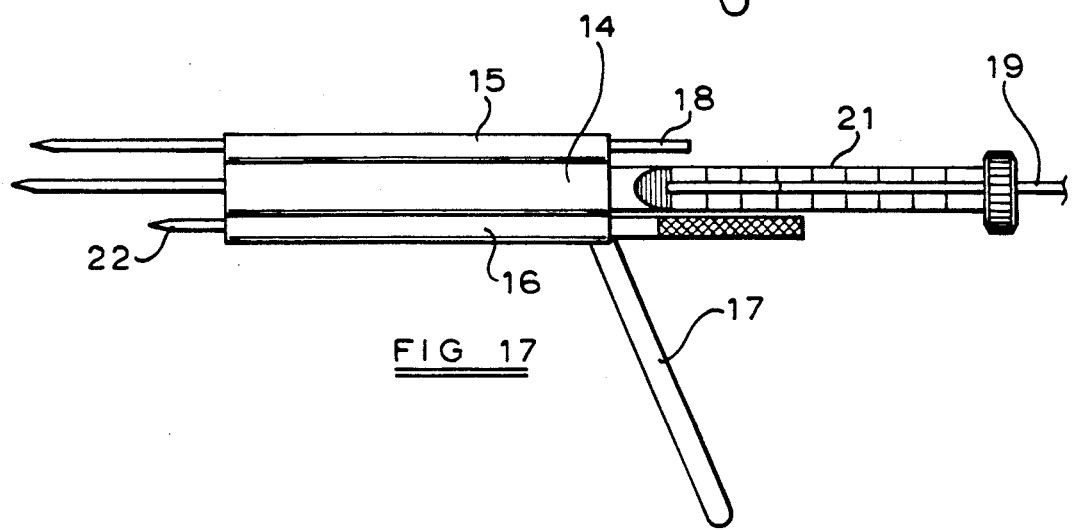
FIG. 17 is a side elevation similar to FIG. 16 but showing the guide anchoring pin of FIG. 9 inserted in a small bore of the guide.
Figure 18:
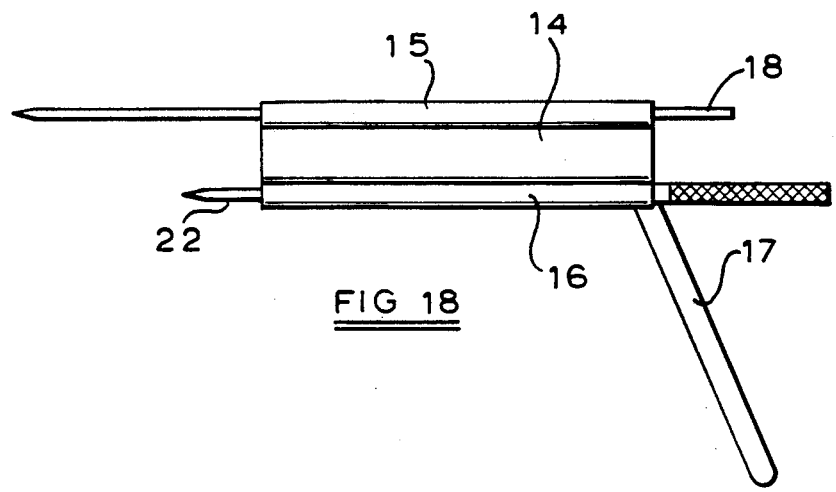
FIG. 18 is a side elevation similar to FIG. 17 but with the main guide wire and the second guide removed.
Figure 19:
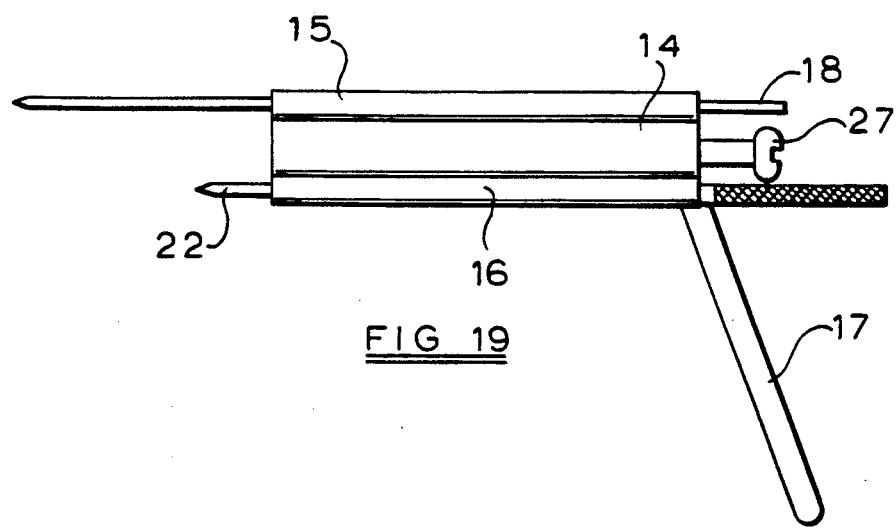
FIG. 19 is a side elevation similar to FIG. 18 with a screw inserted into the larger bore of the main guide.
Figure 20:
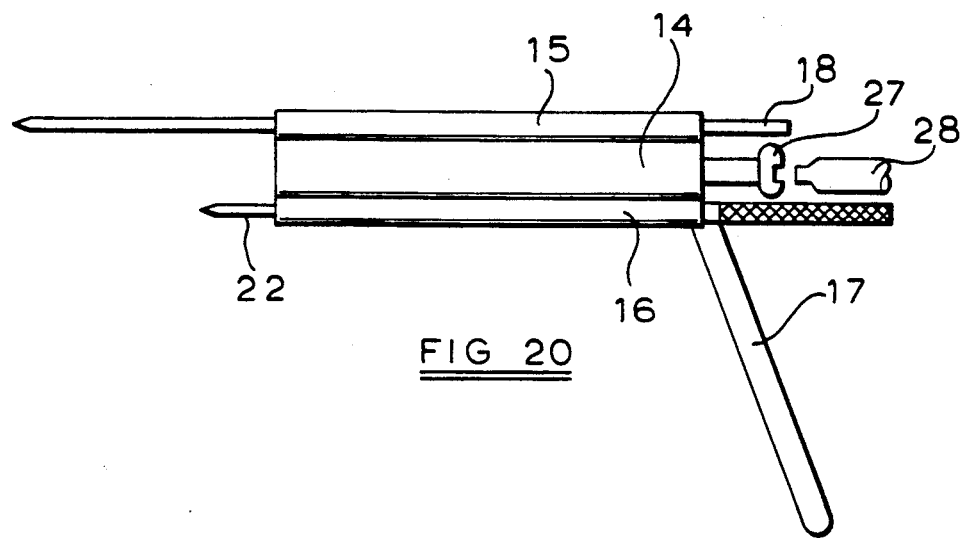
FIGS. 20 and 21 are a side elevation similar to FIG. 19 showing insertion of the screw by means of a screwdriver.
Figure 21:
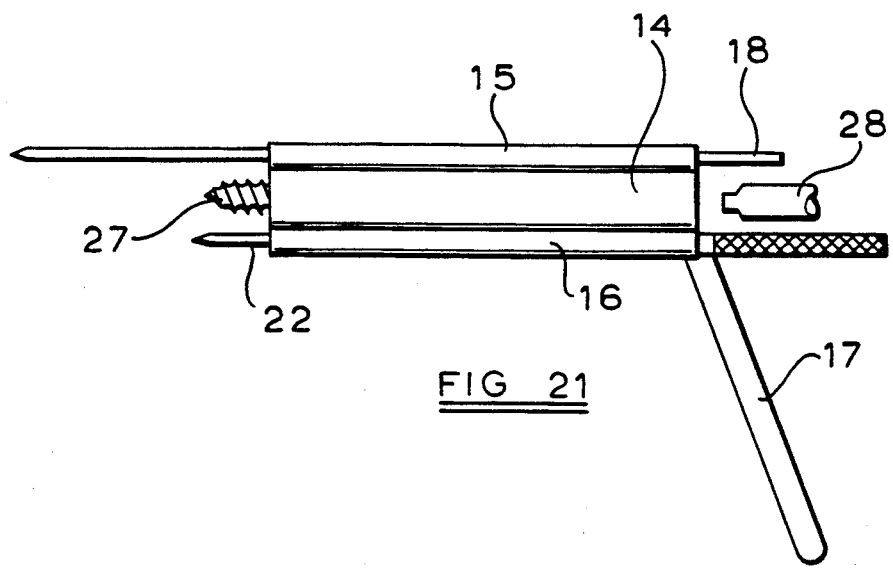

Before a screw is used through the central bore a centering device in the form of the second guide 21 is slidably inserted into the bore of the tube 14, as shown in FIG. 15. The main guide wire 19 is now introduced into the bore of the second guide, as illustrated in FIG. 16, and is driven into the bone to a suitable depth monitored by x-ray. When the correct depth has been achieved, the depth to which the guide wire has traversed the bone can be measured by looking at the mark (20) on the guide wire in relation to the scale on the second guide. In order to secure the guide in position against rotation, the guide anchoring pin 22 is inserted into the bore of the tube 16, as illustrated in FIG. 17, and is driven into the bone. This secures the guide against rotation so that the guide wire and second guide can be removed from the central tube 14. Once the guide wire has been removed, as illustrated in FIG. 18. The 3.2 mm drill is then inserted into the central tube 14, as illustrated in FIG. 12, and is driven to open the outer cortex of the femur to enable the 6.5. mm tap 25 to be inserted into the central tube 14 as illustrated in FIG. 13, to tap an appropriate thread. A 6.5 mm screw 27 of the appropriate length, as previously measured on the scale of the second guide 21, is now inserted into the central tube 14, as illustrated in FIG. 19 and is driven into the bone by a screw driver 28 as illustrated in FIGS. 20 and 21. The screw can only take the position which the guide wire had earlier occupied within the bone.

1, 2, 3 or even 4 screws can be placed in a similar manner by rotating the guide around the first guide wire to take different positions on the outer cortex of the femur. The incision for the operation need be no wider than the width of the guide. To summarise the procedure for use of the guide is as follows.

1. Through a lateral stab incision position the first guide wire 18 in the head 10 of femur passing through the centre of the neck 11 of femur. Centering must be accurate both in the AP and lateral planes.
2. Extend the incision to the width of the guide. Next slide the main guide through its upper bore over this first guide wire 18.
3. Rotate the guide around this first guide wire so that the larger bore of the main guide is directed towards the antero-inferior part of the neck of femur.
4. Place the guide wire centering device/measure 21 through the larger bore of the main guide and push it against the lateral cortex of the femur.
5. Pass the 350 mm×3 mm main guide wire 19 through the centering device 21 and position it through the antero inferior part of the neck into the head 10 of femur. Check the position on the image intensifier. If the position is satisfactory the length of the wire within the bone is noted as indicated by the position of the mark 20 on the measuring scale of the centering device 21.
6. Pass the guide anchoring pin 22 through the lower hole of the main guide and push into the outer cortex of the femur. This will fix the position of the guide.
7. Remove the 350 mm guide wire 19 and its centering device 21. The guide should now stay firmly in place.
8. Now use the 3.2 mm drill 23 to open the hole made by the guide wire 19 on the outer cortex of femur.
9. The sleeve 26 on the tap 25 is next fixed for the length of screw that will be used. This ensures that the tap would cut a thread of exact length within the bone. Slide the tap through the guide and cut the thread in the bone.
10. After the tap is removed pass the measured length of 6.5 mm cancellous screw through the guide and screw it into the head of the femur.
11. Repeat the procedure with the main guide rotated to different positions around the first guide wire. Three or four screws may be placed parallel to each other in this way. It is recommended that two screws are employed close to the calcar (one antero-inferior and another postero-inferior) and a third screw along the superior part of neck of the femur.

Note: if washers are used with the cancellous screws it would be necessary to use a guide where the width of the middle hole is wider than in a standard guide. The width here would be just adequate to allow the washer to pass through rather than the screw head to pass through. All the other instruments like the main guide wire centering device, the drill and the tap which pass through the middle hole of the main guide would also be wider so that they fit snugly inside the middle hole.

Figure 22:
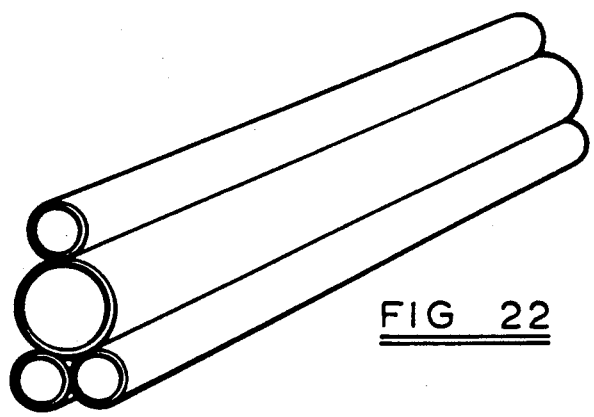
FIG. 22 is an alternative construction of guide.
Figure 23:
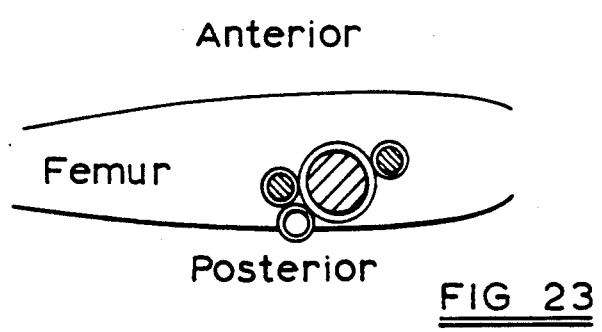
FIG. 23 and FIG. 24 illustrate alternative locational positions when using the guide of FIG. 22.
Figure 24:
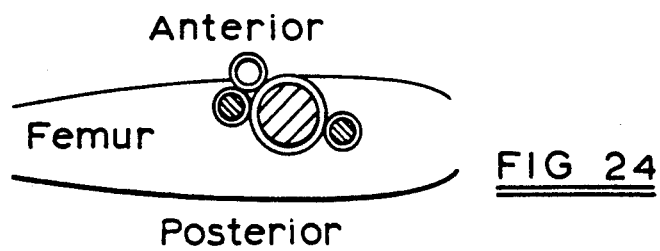

It will be appreciated that modification to the guide are possible without departing from the spirit of this invention for example a guide having four holes instead of three as illustrated in FIG. 22 may be employed. Here there are three outer tubes of small diameter two of which may be employed for the anchoring pin. The advantage of this construction is that when the main guide wire passes through the postero-inferior or antero-inferior part of the neck of femur it is possible that the lowermost hole for the guide anchoring pin may lie in such a position that when the pin is driven in, it may slide over either the posterior or anterior surface of the femur instead of actually penetrating the bone. By using the modified main guide of FIG. 22 it is possible to choose a hole which lies over the bone for the anchoring pin to fix the guide to the bone as shown in FIGS. 23 and 24.

The main guide and the centering device may be made from metal for example stainless steel. Alternatively they may be made from a disposable synthetic material. In this latter case these can then be supplied to operating theatres (with the guide wires and the anchoring pins-made from stainless steel) sterilised and pre-packed for once only use.

The guide of this invention in its preferred form has the following advantages:

1. It simplifies fixation of fracture of the neck of the femur using ordinary cancellous screws (eg 6.5 mm screws). No special screws like cannulated screws are required.
2. The incision for the whole procedure is reduced to the width of the guide—under 2.5 cms even in obese patients.
3. Once a centering guide wire is placed in the centre of the neck of the femur, 2 or 3 cancellous screws can be quickly and accurately positioned around the wire parallel to each other.
4. The centering device for the main guide wire also acts as a measure and gives an instant read out of the size of screw that is required for fixation.
5. When a guide wire is removed and a screw replaced in its position, finding the guide wire entry point on the bone for the screw to enter is no longer difficult as the guide automatically guides the screw into the right position.
6. The guide itself is very simple to use and consists of only a few components.
7. The guide may also be used in other areas like condylar fractures of femur, upper and lower end tibial fractures etc where placing screws parallel to each other is contemplated.

I claim:

1. A method of repairing a fracture of a bone comprising the steps of:
    (a) driving a first guide wire substantially centrally of the bone through the fracture,
    (b) sliding onto the first guide wire a first guide comprising three parallel elongate bores, two of said elongate bores are bores of small diameter, each of said bores of smaller diameter have a diameter substantially equal to the diameter of said first guide wire, one of said elongate bores is a bore of larger diameter than said bores of smaller diameter,
    (c) rotating the first guide around the first guide wire so that the bore of larger diameter is directed towards a suitable area to receive a screw,
    (d) introducing into the bore of larger diameter a second guide of elongate substantially cylindrical cross section having an outer diameter which permits a snug sliding fit in the bore, said second guide having an inside diameter substantially equal to the diameter of said bores of smaller diameter,
    (e) driving a second guide wire into the bone through the bore of the second guide into the fracture to a required depth as defined by a monitoring means,
    (f) noting the required depth, (g) passing a guide anchoring pin through another of said bores of smaller diameter into the bone to secure the first guide against rotation, (h) removing the second guide wire and second guide from the bore of larger diameter, (i) inserting a screw of length equal to said noted depth through the bore of larger diameter and driving said screw into the bone, (j) removing the guide anchoring pin, (k) rotating the first guide around the first guide wire so that the bore of larger diameter is directed towards another suitable area to receive a screw, and (l) repeat steps (d) to (j).

2. The method as claimed in claim 1, wherein step (i) includes introducing a drill into the bore of a larger diameter, said drill having a sleeve which of close sliding fit inside the bore of larger diameter, said sleeve for limiting the depth of initial drilling into the bone to facilitate insertion of the screw.

3. The method as claimed in claim 1, wherein step (i) further includes the steps of:

predrilling of the bone; and introducing into the bore of larger diameter a tap having a sleeve which is in close sliding fit inside the bore and which limits the depth of pretapping of a thread into the bone prior to insertion of the screw.

4. The method as claimed in claim 1, the bone being a neck of a femur, said method further comprising the step of:

inserting a guide wire through an incision into a head of the femur passing substantially centrally through the neck.

5. The method as claimed in claim 4, wherein step (c) includes the step of:

rotating the guide so that the bore of larger diameter is directed towards the antero-inferior part of the neck of the femur.

6. The method as claimed in claim 5, wherein step (g) includes the step of:

driving the anchoring pin into an outer cortex of the femur to secure the first guide against rotation.

* * * * *